US00PP21117P2

(12) United States Plant Patent
Jensen

(10) Patent No.: US PP21,117 P2
(45) Date of Patent: Jun. 29, 2010

(54) *ASTER* PLANTS NAMED 'DASJES'

(50) Latin Name: *Aster novi-belgi*
Varietal Denomination: Dasjes

(75) Inventor: Bent Juhl Jensen, Malling (DK)

(73) Assignee: Gartneriet Raahoj, Malling (DK)

( * ) Notice: Subject to any disclaimer, the term of this patent is extended or adjusted under 35 U.S.C. 154(b) by 0 days.

(21) Appl. No.: 12/380,325

(22) Filed: Feb. 26, 2009

(51) Int. Cl.
*A01H 5/00* (2006.01)

(52) U.S. Cl. ..... Plt./355

(58) Field of Classification Search ..... Plt./355

See application file for complete search history.

(56) References Cited

OTHER PUBLICATIONS

UPOV-ROM GTITM, Plant Variety Database, 2009/05, GTI Jouve Retrieval Software, citation for Aster 'DASJES'.*
Print-out of application number and filing date from Community Plant Variety Office (CPVO) website for corresponding, CPVO application No. 2007/2426 filed Nov. 5, 2007, together with copy of Assignment filed Jan. 23, 2009 (8 pages). (http://www.cpvoextranet.cpvo.europa.eu).

* cited by examiner

*Primary Examiner*—Susan B McCormick Ewoldt
(74) *Attorney, Agent, or Firm*—Foley & Lardner LLP

(57) ABSTRACT

A new distinct cultivar of *Aster* plant named 'DASJES', characterized by its upright and inverted conical plant habit; green and gray-green foliage; decorative, composite-type inflorescence with about 250 white colored ray florets; and only about 5 to 10 disc florets per inflorescence which are white in color with green margin (almost 100% filled capitulae).

3 Drawing Sheets

Latin name of the genus and species of the claimed plant: *Aster novi-belgi* (now *Symphyotrichum novi-belgii*).
Variety denomination: 'DASJES'.

BACKGROUND OF THE INVENTION

The present invention relates to a new and distinct cultivar of *Aster* plant, botanically known as *Aster novi-belgii* (now *Symphyotrichum novi-belgii*) of the Asteraceae family, commonly known as Michaelmas Daisy and New York Aster, and hereinafter referred to by the cultivar name 'DASJES'.

The new *Aster* cultivar is a product of a planned breeding program conducted by the inventor, Bent Juhl JENSEN, in Malling, Denmark. The objective of the breeding program is to develop a new *Aster* variety with uniform plant growth habit, unique floret colors, and good postproduction longevity.

The new *Aster* cultivar originated from a cross made in a controlled breeding program by the inventor on Apr. 1 2005, in Malling, Denmark. The female or seed parent is *Aster novi-belgii* 'WHITE SWAN' (unpatented). The male or pollen parent is *Aster novi-belgii* 'WHITE PRESTIGE' (unpatented, described in terminated CPVO Grant No. 8521). The new *Aster* 'DASJES' was discovered and selected by the inventor as a single flowering plant within the progeny of the stated cross in September of 2006 in a controlled environment in Malling, Denmark. The selection of the new *Aster* 'DASJES' was based on its uniform plant growth habit and desirable inflorescence form and ray floret color.

Asexual reproduction of the new *Aster* cultivar by vegetative tip cuttings was first performed in June of 2006 in Malling, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DASJES', which in combination distinguish this *Aster* as a new and distinct cultivar:

1. Upright and inverted conical plant habit;
2. Green and gray-green foliage;
3. Decorative, composite-type inflorescence with about 250 white colored ray florets; and
4. Only about 5 disc florets per inflorescence which are white in color with green margin (almost 100% filled capitulae).

Plants of the new *Aster* 'DASJES' differ from plants of the parents, *Aster novi-belgii* 'WHITE SWAN' (unpatented) and *Aster novi-belgii* 'WHITE PRESTIGE' (unpatented, described in terminated CPVO Grant No. 8521), in the characteristics described below:

1. Plants of 'DASJES' are more compact than plants of both 'WHITE SWAN' and 'WHITE PRESTIGE';
2. Plants of 'DASJES' produce more ray florets than plants of both 'WHITE SWAN' and 'WHITE PRESTIGE'; and
3. Plants of 'DASJES' produce purely white-colored ray florets whereas plants of 'WHITE SWAN' produce white-colored ray florets and plants of 'WHITE PRESTIGE' produce creamy white-colored ray florets.

Of the many commercial cultivars known to the present inventor, the most similar in comparison to the new *Aster* 'DASJES' is *Aster novi-belgii* 'VICTORIA DIANA' (patented, U.S. Plant Pat. No. 13,359 and CPVO Grant 11802), in the characteristics described in Table 1.

TABLE 1

| Characteristic | New Cultivar 'DASJES' | Comparison Cultivar 'VICTORIA DIANA' (patented) |
|---|---|---|
| Leaf Shape: | Gladiate to oblanceolate | Lanceolate |
| Capitulum Size: | Diameter: 40 mm | Diameter: 32.5 mm |
| Ray Florets | About 250 ray florets per inflorescence, which are oval in shape, with rounded, slightly retuse apex | About 150 ray florets per flower, which are narrowly obovate in shape, with rounded apex |
| Mature Ray Floret Color (upper surface): | Pure White, whiter than RHS 155D, and older petals get a tinge of purple, RHS 75A | Creamy white, RHS 155D |
| Disc Florets: | About 5 disc florets per inflorescence | About 25-35 disc florets per inflorescence |
| Mature Disc Floret Color: | Pure white, whiter than RHS 155D, with green margin, RHS 134D | Yellow-green, RHS 151B |

BRIEF DESCRIPTION OF THE PHOTOGRAPHS

The accompanying photographs illustrate the overall appearance of the new *Aster* 'DASJES' showing the colors as true as is reasonably possible with colored reproductions of this type. Colors in the photographs may differ slightly from the color value cited in the detailed botanical description which accurately describe the color of 'DASJES'.

DETAILED BOTANICAL DESCRIPTION

Figure 1:
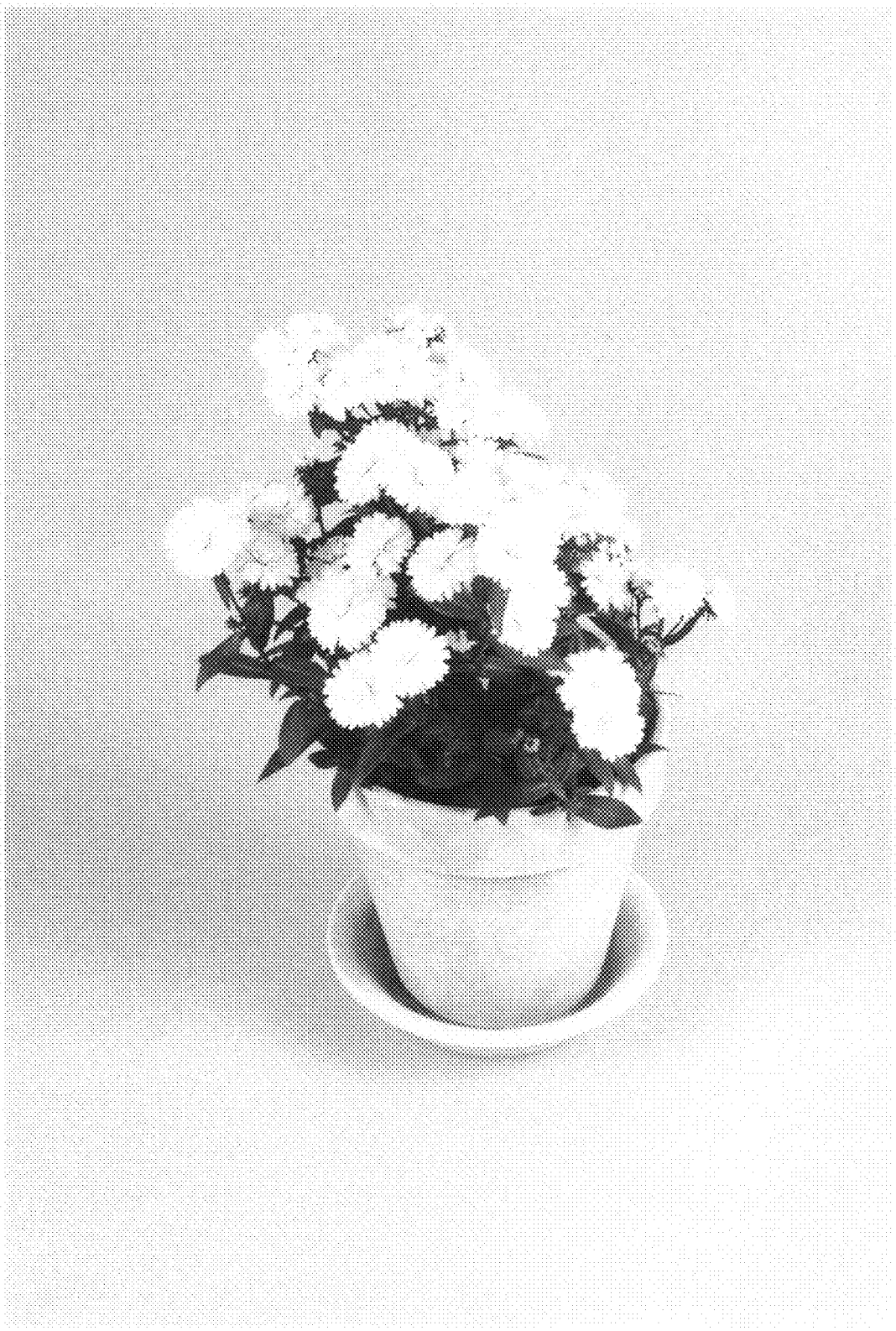
FIG. 1 shows a side view perspective a typical flowering plant of 'DASJES' in a 9.5 cm pot, at 10 weeks of age after planting.
Figure 2:
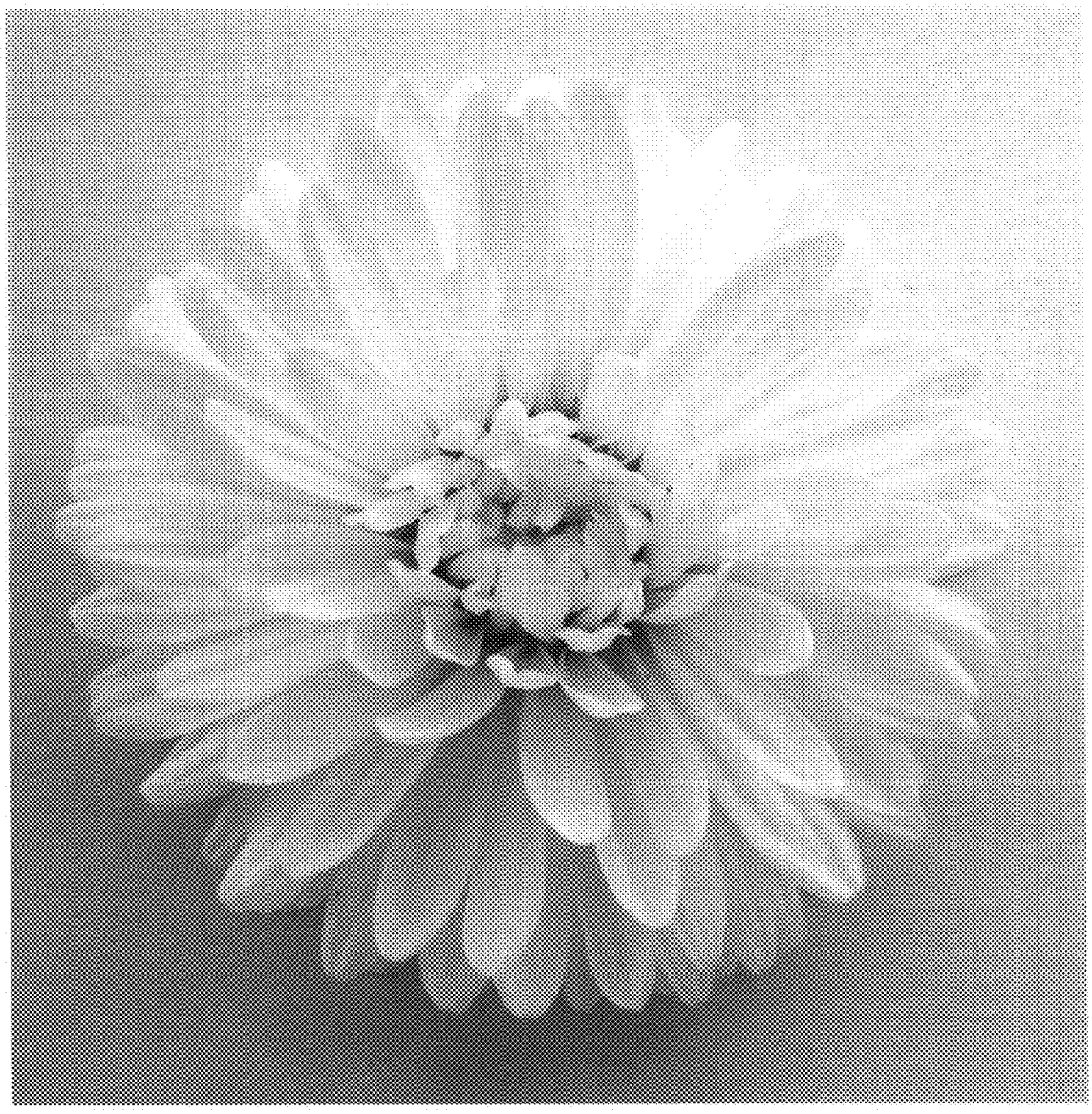
FIG. 2 shows a close-up view perspective of a typical mature inflorescence of 'DASJES', at 10 weeks of age after planting.
Figure 3:
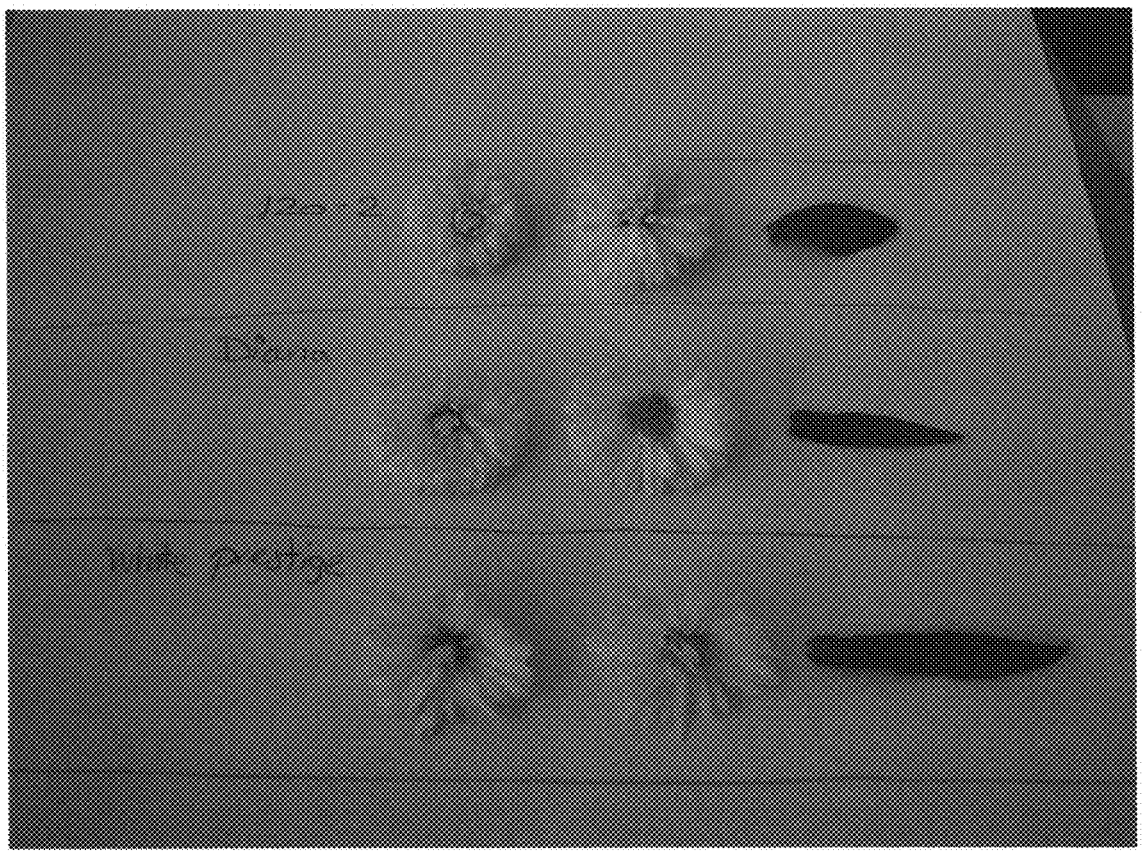
FIG. 3 shows a close-up comparison view of a typical mature inflorescence and leaf of: 1) the new *Aster* 'DASJES' (referenced by breeder designation 120-2), compared to 2) the comparison cultivar *Aster* 'VICTORIA DIANA' (referenced by DIANA), and 3) the male parental cultivar Aster 'WHITE PRESTIGE'.

The new *Aster* 'DASJES' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Aster* 'DASJES' as grown in a glass-covered greenhouse in Mailing, Denmark, under conditions which closely approximate those generally used in commercial practice. 'DASJES' plants were grown in 9.5 cm pots in a heated and lighted glass-covered greenhouse with the day temperatures ranging from 18° C. to 20° C. and the night temperature averaging 18° C. 'DASJES' plants are grown under long day (20 hour) photoperiodic treatments for five weeks, followed by short day (12 hour) photoperiodic treatments for five weeks. During the long day (20 hour) photoperiodic treatments, if ambient light level falls below +50 $Wm^2$, a supplementary light at +200 $Wm^2$ is applied. 'DASJES' plants 'DASJES' plants were pinched once, and treated twice with the growth retardant Daminozide.

Color references are made to The Royal Horticultural Society Colour Chart (R.H.S.), 4th Edition, except where general colors of ordinary significance are used. Color values were taken under daylight conditions in Malling, Denmark. The age of the 'DASJES' plants shown in the photographs and described herein is about 10 weeks.

Classification:

*Botanical.*—*Aster novi-belgii* (now *Symphyotrichum novi-belgii*).

Parentage:

*Female or seed parent.*—*Aster novi-belgii* 'WHITE SWAN' (unpatented).

*Male or pollen parent.*—*Aster novi-belgii* 'WHITE PRESTIGE' (unpatented, described in terminated CPVO Grant No. 8521).

Propagation:

*Type.*—Vegetative tip cuttings.

*Time and temperature to initiate roots.*—Summer: About 12 days at 21° C. Winter: About 13 days at 21° C.

*Rooting habit.*—Fine, fibrous and freely branching.

*Root color.*—Gray-white, close to RHS 156D.

Plant description:

*General appearance and form.*—Herbaceous, decorative-type potted or bedding plant with upright plant habit. *Aster* inflorescences in composite heads.

*Growth and branching habit.*—Stems upright; inverted conical plant habit. Appropriate for 9 cm to 15 cm containers.

*Growth rate/vigor.*—Vigourous.

*Plant height* (*soil level to top of plant plane*).—About 16 cm.

*Plant width* (*spread*).—About 23 cm.

*Crop time to produce a mature flowering plant.*—After rooting, about 10 weeks are required to produce finished flowering plants in 9.5 cm pots.

Branches:

*Number of branches per plant.*—About 10, with 3 cuttings per pot.

*Quantity of buds and inflorescence per lateral stem.*—About 2 to 6, buds continue to develop when dead flowers are removed.

*Branching habit.*—Freely after pinching.

*Length.*—About 15 cm (including flowers).

*Diameter.*—About 3 mm.

*Internode length.*—About 9 mm. Range about 7 mm to 13 mm.

*Strength.*—Strong.

*Aspect.*—Upright.

*Texture.*—Hispidolous with 3–4 longitudinal furrows.

*Color.*—Green, RHS 137C.

Foliage description:

*Quantity per branch.*—About 10 to 14.

*Arrangement.*—Single, alternate , sessile.

*Length.*—Up to 4 cm.

*Width.*—Up to 12 mm.

*Overall shape of leaf.*—Gladiate to oblanceolate.

*Shape at apex.*—Acute.

*Shape at base.*—Decurrent, auriculate ½ clasping.

*Margin.*—Entire.

*Texture.*—Glabrous, smooth, leathery.

*Pubescence.*—None.

*Color of developing foliage.*—Upper surface: Green, RHS 137A. Under surface: Gray-green, RHS 189A.

*Color of mature foliage.*—Upper surface: Green, RHS 137A. Under surface: Gray-green, RHS 189A.

*Venation pattern.*—None, but prominent central abaxial vein.

*Venation color.*—Upper surface: Green, RHS 137A. Under surface: Yellow-green, RHS 146B.

Inflorescence description:

*Appearance.*—Terminal and axillary composite inflorescences held above and beyond the foliage, with about 250 lanceolate-shaped ray florets and only about 5 disc florets; ray and disc florets arranged acropetally on a capitulum. Inflorescences face upright and form is capitulate in corymbose stands.

*Natural flowering season.*—Under natural season conditions, plants flower in late summer through autumn in Denmark. Season can be extended by vernalization and long day treatments.

*Time to flower.*—About 5 to 6 weeks (longevity of individual inflorescences is dependent on temperature and light conditions).

*Postproduction longevity.*—Inflorescences maintain good color and substance for about 27 to 32 days on the plant when in an indoor environment, and may keep longer if temperatures are maintained below 20° C. Inflorescences persistent.

*Quantity of inflorescences.*—About 40 to 50 buds and open inflorescences per plant.

*Fragrance.*—Faint.

*Bud.*—Rate of opening: About 10 per week, for 3 weeks after induction. Length: Up to 7 mm. Diameter: Up to 7 mm. Shape: Globular. Texture: Glabrous. Color: Green, RHS 137C.

*Peduncle.*—Length: Up to 4 cm. Diameter: 1 mm. Appearance and angle: About 70° from vertical. Strength: Strong. Texture: Glabrous. Color: Green, RHS 134C.

*Inflorescence.*—Inflorescence (corymb) (height): About 6 to 8 cm. Inflorescence (corymb) diameter About 4 to 6 cm. Capitulum height: About 1.5 cm. Capitulum diameter: About 4 cm.

*Quantity of flowers (capitulae) per inflorescence (corymb).*—About 10 to 12 capitulae.

*Ray florets.*—Arrangement and quanity: Imbricate, about 250 ray florets per capitulum in 9 to 12 whorls of ray florets (depending on light and temperature conditions). Orientation: Initially upright, later mostly horizontal. Aspect: Straight to slightly involute. Appearance: Lanceolate, but sides turn inward (involute) Length: About 8 mm. Width: About 3 mm. Overall shape: Oblong, and developing slightly involute Shape at apex: Rounded, slighlty retuse. Shape at base: Fused. Margin: Entire. Texture: Upper and under surfaces: Smooth, glabrous, silky. Pubescence: Subtended by numerous short, about 2 mm, white hairs. Color (when opening and fully opened): Upper and under surfaces: Pure white, whiter than RHS 155D. Fading: Yes, older ray florets get a tinge of purple, RHS 75A, and wither to gray-brown, RHS N199C.

*Disc florets.*—Arrangement: About 5 disc florets, massed at center of capitulum. Length: About 2 mm. Width: About 1 mm. Disc area diameter: About 2 mm. Overall shape: Tubular, elongated. Shape at apex: Acute. Shape at base: Fused to tube. Margin: Entire. Texture: Upper and under surfaces: Scale-like, parchment thin. Pubescence: Subtended by numerous short, about 2 mm, white hairs. Color (when opening): Upper and under surfaces: Pure white, whiter than RHS 155D, with green margin, RHS 134D. Color (when fully opened): Upper and under surfaces: Pure white, whiter than RHS 155D, with green margin, RHS 134D.

*Phyllaries.*—Quantity per inflorescence: Involucre, about 40 to 50. Length: About 3 to 6 mm. Width: About 1 to 2 mm. Overall shape: Tubular, elongated. Apex shape: Acute. Base shape: Fused lanceloate. Margin: Entire. Texture: Hairy, setulose edges, verrucose abaxial surface. Color (immature): Upper surface: Green, RHS 137B. Under surface: Green, RHS 137D. Color (immature): Upper surface: Green, RHS 137A. Under surface: Green, RHS 137B.

Reproductive organs:

*Androecium (on disc florets only).*—Stamen number: 1 per floret; fused around style. Stamen length: About 0.5 mm. Anther shape: Narrowly cylindrical, somewhat fused. Anther length: About 0.1 mm. Anther color: Yellow, RHS 8B. Pollen amount: Scarce. Pollen color: Yellow, RHS 8A.

*Gynoecium (on disc and ray florets).*—Pistil number: 1 per floret. Pistil length: About 2 mm. Stigma shape: Cleft. Stigma length: About 0.5 mm. Stigma color: White, RHS N155C. Style length: About 1 mm. Style color: White, RHS N155D. Ovary diameter: About 1 mm. Ovary color: White, RHS N155D.

Seed: None observed.

Fruit: None observed.

Disease/pest resistance: Resistance to pathogens and pests common to *Asters* has not been observed on plants grown under commercial greenhouse conditions.

Disease/pest susceptibility: Resistance to pathogens and pests common to *Asters* has not been observed on plant grown under commercial green house conditions, except mildew after flowers wilt.

High temperature tolerance: Not specifically tested, but if enough water is available, tolerant up to 35° C.

Low temperature tolerance: Not specifically tested, but if enough water is available, tolerant to −15° C.

I claim:

1. A new and distinct cultivar of *Aster* plant named 'DASJES', as illustrated and described herein.

* * * * *